(12) United States Patent
Vaingast et al.

(10) Patent No.: US 8,585,580 B2
(45) Date of Patent: Nov. 19, 2013

(54) INFLATABLE MEDICAL IMPLANT SYSTEM

(75) Inventors: Shay Moshe Vaingast, Ganei Tikva (IL); Charles C. Kuyava, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 519 days.

(21) Appl. No.: 12/864,315

(22) PCT Filed: Jan. 22, 2009

(86) PCT No.: PCT/US2009/031669
§ 371 (c)(1),
(2), (4) Date: Sep. 14, 2010

(87) PCT Pub. No.: WO2009/094431
PCT Pub. Date: Jul. 30, 2009

(65) Prior Publication Data
US 2011/0015738 A1    Jan. 20, 2011

Related U.S. Application Data

(60) Provisional application No. 61/023,015, filed on Jan. 23, 2008.

(51) Int. Cl.
*A61F 2/02* (2006.01)
(52) U.S. Cl.
USPC .......................................................... 600/37
(58) Field of Classification Search
USPC ............ 600/29–31, 37–39, 41; 128/897–899
See application file for complete search history.

(56) References Cited

U.S. PATENT DOCUMENTS 4,705,518 A   11/1987   Baker et al.
6,243,607 B1   6/2001   Mintchev et al.
(Continued)

FOREIGN PATENT DOCUMENTS

WO        0000082 A1    1/2000
WO     2007097994 A2    8/2007

OTHER PUBLICATIONS

Yamamoto et al., "Optimal parameters for effective electrical stimulation of the anal sphincters in a child with fecal incontinence: preliminary report," Pediatr Surg Int (1993) 8:132-137.

(Continued)

*Primary Examiner* — Christine Matthews
*Assistant Examiner* — Joshua D Lannu
(74) *Attorney, Agent, or Firm* — Brian D. Kaul; Westman, Champlin & Koehler, P.A.

(57) ABSTRACT

Embodiments of an inflatable medical implant system configured for implantation in a patient to treat a condition of the patient comprise a first fluid path, an inflatable implant, an electric pump, a controller, and an implantable power supply that provides electrical power to the pump. The inflatable implant is in fluid communication with the first fluid path and is configured to serve a medical purpose. The electric pump is in fluid communication with the first fluid path. The controller is electrically coupled to the pump and is configured to activate the pump to drive a flow of fluid through the first fluid path. In one embodiment, the inflatable implant comprises and inflatable cuff or a penile prosthesis. Additional embodiments of the invention are directed to methods of operating embodiments of the inflatable medical implant system.

11 Claims, 8 Drawing Sheets

(56) References Cited

U.S. PATENT DOCUMENTS

| | | |
|---|---|---|
| 6,612,977 B2 | 9/2003 | Staskin et al. |
| 6,659,937 B2 | 12/2003 | Polsky et al. |
| 6,911,003 B2 | 6/2005 | Anderson et al. |
| 7,011,622 B2 | 3/2006 | Kuyava et al. |
| 7,613,516 B2 | 11/2009 | Cohen et al. |
| 2002/0161382 A1 | 10/2002 | Neisz et al. |
| 2003/0028232 A1 | 2/2003 | Camps et al. |
| 2004/0039453 A1 | 2/2004 | Anderson et al. |
| 2005/0240144 A1* | 10/2005 | Wassemann et al. ........... 604/20 |
| 2005/0256367 A1 | 11/2005 | Banik |
| 2006/0135845 A1 | 6/2006 | Kuyava et al. |
| 2007/0015954 A1 | 1/2007 | Dlugos |
| 2007/0021650 A1 | 1/2007 | Rocheleau et al. |
| 2007/0156013 A1* | 7/2007 | Birk ................................ 600/37 |
| 2007/0260288 A1 | 11/2007 | Gross |
| 2010/0076254 A1 | 3/2010 | Jimenez et al. |
| 2010/0160716 A1 | 6/2010 | Snow |

OTHER PUBLICATIONS

Yamanishi et al., "Electrical Stimulation for Stress Incontinence", Int. Urogynecol J (1998) 9:281-290 Springer-Verlag London Ltd.

* cited by examiner

INFLATABLE MEDICAL IMPLANT SYSTEM

CROSS-REFERENCE TO RELATED APPLICATION

This Application is a Section 371 National Stage Application of International Application No. PCT/US2009/031669, filed Jan. 22, 2009 and published as WO 2009/094431 on Jul. 30, 2009, and claims the benefit of U.S. Provisional Application Ser. No. 61/023,015 filed Jan. 23, 2008 under 35 U.S.C. §119(e). Each of the above-referenced applications are incorporated herein by reference in their entirety.

FIELD OF THE INVENTION

Embodiments of the invention generally relate to implantable medical devices and, more specifically, to an inflatable implant system comprising an inflatable implant and an electric pump.

BACKGROUND

Common inflatable implants include prosthetic sphincters and penile prostheses. The inflatable sphincter typically includes an inflatable cuff that is placed around a duct of the patient. When the cuff is inflated, it constricts the duct and inhibits the flow of material through the duct. Deflation of the cuff allows material to pass through the duct. Such artificial sphincters are often used to treat urinary and fecal incontinence. Inflatable penile prostheses typically include a pair of inflatable cylinders which are implanted into the corpus cavernosae of the patient. The cylinders are inflated to produce the desired penis rigidity for a normal erection and deflated to return the penis to a flaccid state. Exemplary inflatable implant systems of the prior art utilizing an inflatable sphincter and inflatable penile prostheses are respectively described in U.S. Pat. No. 7,011,622 and U.S. Patent Application Publication No. 2006/0135845, both of which are incorporated herein by reference in their entirety.

FIG. 1 is a simplified diagram of an inflatable implant system 100 of the prior art that is commonly used with one or more inflatable implants 102 in the form of an artificial sphincter or cuff, or penile prosthesis. The system 100 includes the inflatable implant 102, a manual pump 104 and a fluid reservoir 106. The inflatable implant 102 is implanted in the patient in accordance with its designed application. The manual pump 104 is generally implanted in the scrotum of the patient and the reservoir 106 is implanted in the abdomen of the patient. The device 100 forms a closed-loop system that can be filled with a suitable fluid, such as saline.

The inflatable implant 102 is in fluid communication with the pump 104 through tubing 108, and the pump 104 is in fluid communication with the reservoir 106 through tubing 110. Fluid flows between the cuff 102 and the reservoir 106 through the tubing 108, the tubing 110 and the pump 104 to inflate and deflate the cuff 102.

The pump 104 includes a control assembly 112 for controlling the flow of fluid to and from the cuff 102. The pump 104 is operated by manually compressing a pump chamber 114. The control assembly 112 can be configured to direct the fluid from the chamber 114 into the reservoir 106 through the tubing 110 in response to the compression of the chamber 114, which pressurizes the reservoir 106 and deflates the inflatable implant 102. After the pressurization of the reservoir 106, the control assembly 112 gradually releases fluid from the reservoir into the inflatable implant 102 to slowly re-inflate the implant 102. Thus, the fluid in the reservoir 106 is pressure-driven through the tubing 110, the control assembly 112, and the tubing 108, and into the inflatable implant 102 to inflate the implant 102 until the pressures in the reservoir 106 and the inflatable implant 102 equalize. This configuration is typical for inflatable implants in the faun of artificial sphincters. The pressurized state of the reservoir 106 can be preserved through the actuation of a button 115 of the control assembly 112 by the patient.

The control assembly 112 can also be configured to direct the fluid from the chamber 114 into the inflatable implant 102 to inflate the implant 102. This configuration is typical for inflatable implants in the form of penile prostheses. The pressurized state of the inflatable implant 102 can be released through the actuation of the button 115 of the control assembly 112 by the patient. This allows the fluid in the inflatable implant 102 to be pressure-driven through the tubing 108, the control assembly 112, and the tubing 1110, and into the reservoir 106 until the pressures in the reservoir 106 and the inflatable implant 102 equalize.

The compression of the pump chamber 114 and actuation of the button 115 for both the inflatable sphincter and penile prostheses forms of the system 100 require manual dexterity that some patients will not be able to achieve.

Accordingly, some patients who could benefit from the system 100 are not suitable candidates for receiving it.

SUMMARY

Embodiments of the present invention are directed to an inflatable medical implant system configured for implantation in a patient to treat a condition of the patient. One embodiment of the system comprises a first fluid path, an inflatable implant, an electric pump, a controller, and an implantable power supply that provides electrical power to the pump. The inflatable implant is in fluid communication with the first fluid path and is configured to serve a medical purpose. The electric pump is in fluid communication with the first fluid path. The controller is electrically coupled to the pump and is configured to activate the pump to drive a flow of fluid through the first fluid path. In one embodiment, the inflatable implant comprises an inflatable cuff or a penile prosthesis.

In one embodiment, the system further comprises a second fluid path in fluid communication with the inflatable implant, a third fluid path in fluid communication with the pump, a reservoir in fluid communication with the second fluid path and the third fluid path, and a valve. The valve is positioned in line with the second fluid path between the inflatable implant and the reservoir. The valve includes an opened position, in which fluid is free to travel between the reservoir and the inflatable implant through the second fluid path, and a closed position, in which fluid is blocked from traveling between the reservoir and the inflatable implant through the second fluid path. In one embodiment, the controller selectively actuates the valve to the opened and closed positions.

Another embodiment of the invention is directed to a method of operating embodiments of the inflatable medical implant system. In the method, the medical implant system is implanted in a patient. The inflatable implant is inflated either by placing the valve in the opened position and driving a flow of fluid from the reservoir into the inflatable implant through the second fluid path in response to a pressure difference between the reservoir and the inflatable implant, or by placing the valve in the closed position and driving a flow of fluid from the first fluid path into the inflatable implant using the pump. In one embodiment, the inflatable implant is deflated either by placing the valve in the closed position and driving a flow of fluid from the inflatable implant into the first fluid path using the pump, or by placing the valve in the opened position and driving a flow of fluid from the inflatable implant into the reservoir through the second fluid path in response to a pressure difference between the implant and the reservoir. A medical condition of the patient is treated in response to the inflating and/or deflating of the inflatable implant.

Other features and benefits that characterize embodiments of the present invention will be apparent upon reading the following detailed description and review of the associated drawings.

DETAILED DESCRIPTION OF ILLUSTRATIVE EMBODIMENTS

Figure 1:
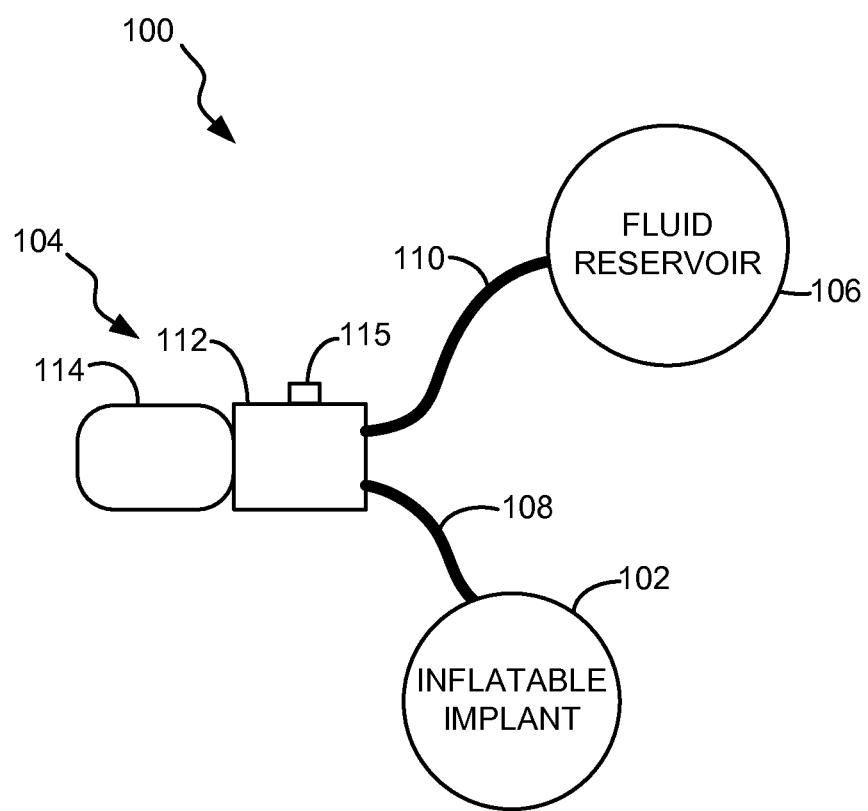
FIG. 1 is a simplified diagram of an inflatable implant system in accordance with the prior art.
Figure 2:
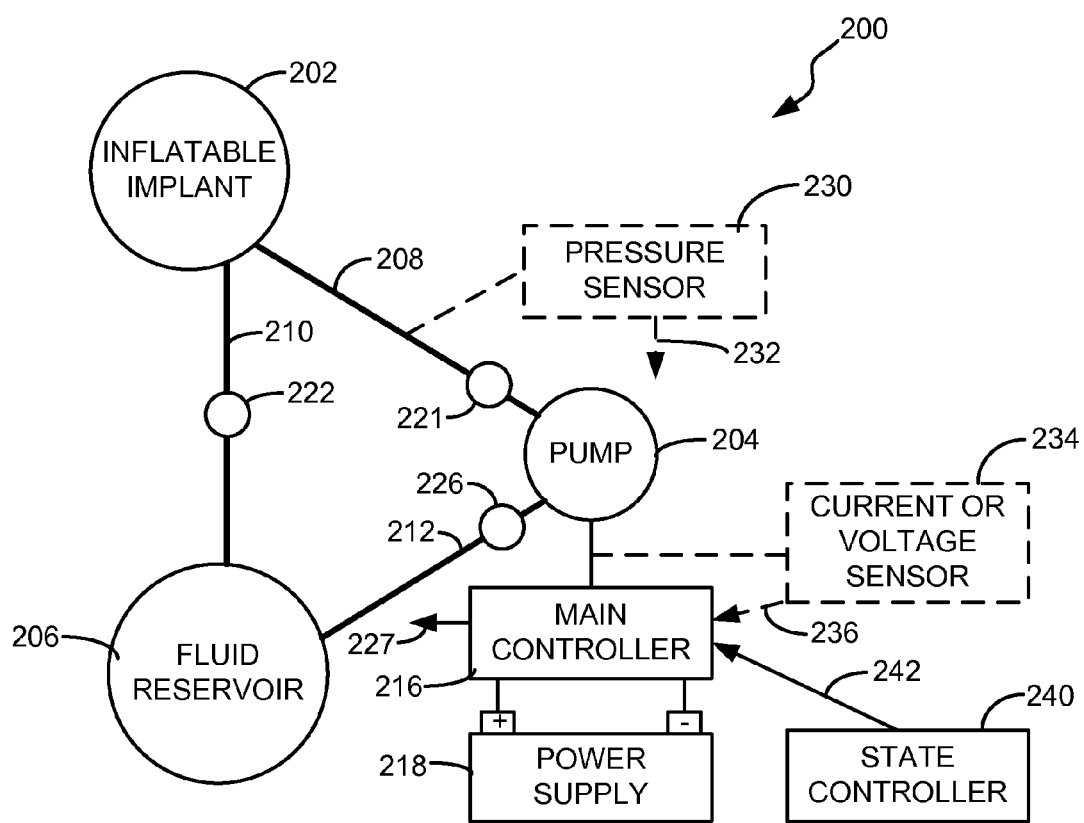
FIG. 2 is a simplified diagram of an inflatable medical implant system in accordance with embodiments of the invention.

Embodiments of the present invention are directed to an inflatable medical implant system that can be implanted in a patient to treat a condition of the patient. FIG. 2 is a simplified diagram of an inflatable medical implant system 200 in accordance with embodiments of the invention. The system 200 includes an inflatable implant 202, an electric pump 204 and a fluid reservoir 206. The system 200 is a closed loop system, in which a fluid, such as saline, flows between the reservoir 206 and the inflatable implant 202 to place the implant 202 in either an inflated condition or a deflated condition in order to treat the condition of the patient.

The inflatable implant 202 is configured to serve a medical purpose and represents one or more inflatable components that are configured for implantation in a patient. The "medial purpose" of the implant 202 means that it is used to facilitate the treatment of a medical condition of the patient.

In one embodiment, the inflatable implant 202 comprises one ore more artificial sphincters or cuffs that can each be implanted around a duct of the patient and control the flow of material through the duct of the patient in order to treat a medical condition. The artificial sphincter or cuff inhibits the flow of material through the duct when inflated, and allows the flow of material through the duct when deflated. Such artificial sphincters can be used to treat numerous medical conditions. For instance, the artificial sphincter can be placed around the urethra of the patient to treat urinary incontinence, the artificial sphincter can be placed around the rectum or colon of the patient to treat fecal incontinence, the artificial sphincter can be used as a gastric cuff to control weight loss dynamically, the artificial sphincter can be used as a stoma clamp/cuff in case of partial intestine or colon removal. Embodiments of the invention include the implantation of the system 200 in a patient to treat at least one of the above-described conditions in a male or female patient.

In accordance with another embodiment, the inflatable implant 202 is in the form of a penile prosthesis. As mentioned above, such an inflatable implant 202 is implanted in one of the corpus cavernosa of the male patient and is inflated to produce the desired penis rigidity of a normal erection and deflated to return the penis to a flaccid state.

The inflatable implant 202 can also take on other forms that can be implanted in the patient and used to treat a medical condition of the patient.

In one embodiment, the system 200 includes a first fluid path 208, a second fluid path 210, and a third fluid path 212. The first fluid path 208 fluidically couples the inflatable implant 202 to the pump 204. The second fluid path 210 fluidically couples the inflatable implant 202 to the reservoir 206. The third fluid path 212 fluidically couples the pump 204 to the reservoir 206. The inflatable implant 202, the pump 204, the reservoir 206 and the fluid paths 208, 210 and 212, form a closed system that contains a fluid, such as saline.

Additional embodiments of the system 200 include a controller 216 and a power supply 218, such as an implantable battery. The power supply 218 can supply power to the controller 216, the pump 204 and other components of the system 200 that require electrical power, such as valves. In one embodiment, the controller 216 operates to selectively activate or deactivate the pump 204 in accordance with conventional techniques, to drive a flow of the fluid through the first fluid path 208. As discussed in greater detail below, in accordance with some embodiments, the activation of the pump 204 drives the flow of fluid out of the inflatable implant 202 and through the first fluid path 208, while other embodiments drive the flow of fluid from the first fluid path 208 into the inflatable implant 202. The control of the pump 204 by the controller 216 can be accomplished in accordance with conventional methods. In one embodiment, the power supply 218 was electrically coupled to the controller 216, which operates to selectively deliver electrical power to activate the pump 204, or cut off power to the pump 204 to deactivate the pump 204. Other suitable configurations can also be used.

One exemplary control electronic is a piezoelectric pump (e.g., microdiaphragm pump), such as those supplied by ThinXXS including the MDP2205 microdiaphragm pump. The controller 216 also includes any necessary control electronics, such as an electronic pump driver, which may be required due to cyclic voltage excursions at various frequencies in accordance with the design of the pump 204.

Embodiments of the system 200 include one or more valves, such as valve 221 in line with the first fluid path 208, valve 222 in line with the second fluid path 210, and valve 226 in line with the third fluid path 212. The valves of the system 200 include any valve type that is suitable for performing the desired functions described below, such as latching solenoid valves that are actuated through electrical control signals from the controller 216, check valves, and combinations thereof (e.g., one-way latching solenoid valves), for example. One suitable latching solenoid valve that could be used is, for example, the series 120 two-way solenoid valve produced by Lee Company. Embodiments of the valves 221 and 226 also include valves that are integrated with the pump 204.

Specific embodiments of the valves 221, 222 and/or 226 include valves that are actuated between an opened position, in which fluid is free to travel in the respective fluid path, and closed positions in which fluid is blocked from traveling in the respective fluid path. For instance, one embodiment of valve 221 can have an opened position, in which fluid is in which fluid is free to travel between the pump 204 and the inflatable implant 202 through the first fluid path 208, and a closed position, in which fluid is blocked from traveling between the pump 204 and the inflatable implant 202 through the first fluid path 208. Similarly, one embodiment of valve 222 has an opened position, in which fluid is free to travel between the reservoir 206 and the inflatable implant 202 through the second fluid path 210, and a closed position, in which fluid is blocked from traveling between the reservoir 206 and the inflatable implant 202 through the second fluid path 210. Also, one embodiment of valve 226 has as an opened position, in which fluid is free to travel between the reservoir 206 and the pump 204 through the third fluid path 212, and a closed position, in which fluid is blocked from traveling between the reservoir 206 and the pump 204 through the third fluid path 212. In one embodiment, two or more of the valves 221, 222 and 226 are integrated into a single assembly.

In one embodiment, the controller 216 selectively actuates the valves 221, 222 and/or 226 between opened and closed positions using appropriate electrical control signals 227. In one embodiment the control signals 227 from the controller 216 to one or more of the valves 221, 222 and/or 226 comprise a short voltage pulse to switch the valve between the opened and closed positions. Such a short switching voltage pulse means that the valves do not have to be continuously energized, thus using little energy from the power supply 218 and prolonging the life of the implantable power supply 218.

Embodiments of the system 200 include at least two configurations, each comprising a filling state, in which fluid is driven into the inflatable implant 202 to inflate the implant 202, and an emptying state, in which fluid is driven from the inflatable implant 202 to deflate the implant 202. When the inflatable implant 202 is in the form of a cuff, the inflation of the cuff responsive to the filling state causes the cuff to constrict the duct it surrounds to prevent the flow of material through the duct and prevent, for example, urinary incontinence. The deflation of the cuff responsive to the emptying state removes the constriction of the duct and allows material to flow through the duct to allow the patient to urinate, for example. When the inflatable implant 202 is in the form of a penile prosthesis, the inflation of the penile prosthesis responsive to the filling state causes the penile prosthesis to expand the corpus cavernosa to generate an erection, and the deflation of the penile prosthesis responsive to the emptying state allows the corpus cavernosa to contract to place the penis in the flaccid state.

In a first configuration, the inflatable implant 202 is inflated with fluid by driving a flow of fluid from the reservoir 206, through the second fluid path 210 and into the inflatable implant 202 in response to a pressure difference between the fluid reservoir 206 and the inflatable implant 202, and the system 200 deflates the inflatable implant 202 by driving a flow of fluid from the inflatable implant 202 and into the first fluid path 208 using the pump 204. In accordance with a second configuration, the system 200 inflates the inflatable implant 202 by driving a flow of fluid from the first fluid path 208 into the inflatable implant 202, and the system 200 deflates the inflatable implant 202 by driving a flow of fluid from the inflatable implant 202, through the second fluid path 210 and into the reservoir 206 in response to a pressure difference between the inflatable implant 202 and the reservoir 206.

Figure 3:
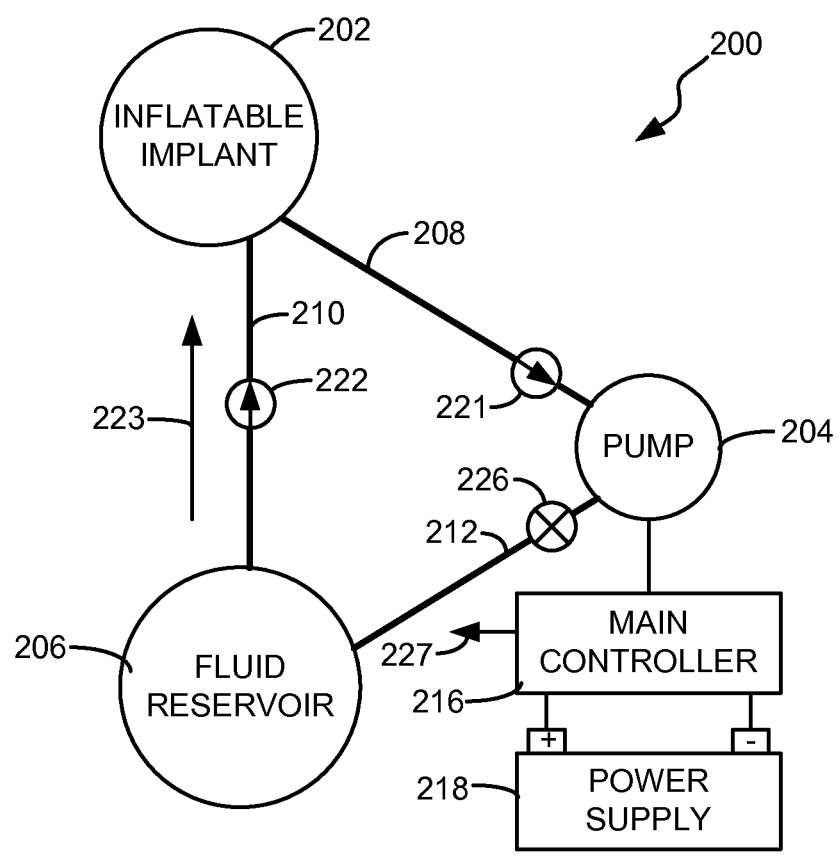
FIGS. 3 and 4 are simplified diagrams of a first configuration of the inflatable medical implant system in a filling state and an emptying state, respectively, in accordance with embodiments of the invention.

Embodiments of the filling and emptying states of the first configuration will be respectively described with reference to the simplified diagrams of the system 200 provided in FIGS. 3 and 4. In one embodiment of the filling state, the pump 204 is deactivated and the valve 222 is set to the opened position, in which fluid from the reservoir 206 is allowed to travel through the second fluid path 210 in the direction of arrow 223 to the inflatable implant 202, as indicated in FIG. 3. This flow of fluid is responsive to a pressure difference between the reservoir 206 and the inflatable implant 202. The flow of fluid through the first fluid path is blocked by the valve 221 or 226 while the system 200 is in the filling state. When the system is pressure balanced at the pressure of the reservoir 206 (i.e., system quiescent state), the inflatable implant 202 reaches an inflated state having a desired inflated pressure or volume.

In one embodiment, at least one of the valves 221 or 226 has the opened and closed states described above. In FIG. 3, valve 226 is illustrated as being in the closed position during the filling state of the system 200. In accordance with another embodiment, one or both of the valves 221 and 226 are check valves that only allow fluid to flow in the first and second fluid paths in the direction indicated by their arrows (FIG. 4), respectively, when the pressure drop across the valves exceeds a threshold value that is greater than the desired maximum inflated pressure of the implant 202. In one embodiment, the valve 222 does not comprise a one-way check on the flow of fluid when in the opened position, which would produce a significant pressure drop across the valve 222. Thus, the opened position of the valve 222 substantially allows for unrestricted flow of fluid from the reservoir 206 to the inflatable implant 202 via the second fluid path 210. Such an unrestricted flow allows for faster filling of the inflatable implant 202 and faster response to abdominal disturbances.

In the event of an abdominal disturbance in the patient that results in increased abdominal pressure, the increased abdominal pressure acts on the reservoir 206 to increase its internal pressure. In response to this pressure disturbance to the filling state of the system 200, additional fluid is transferred from the reservoir 206 to the inflatable implant 202 through the second fluid path 210, which increases the pressure within the inflatable implant 202 briefly to further expand the inflatable implant 202. When the duct is the urethra of the patient, an abdominal disturbance may increase the pressure on the bladder of the patient. The abdominal disturbance will also cause a similar increase in pressure to the reservoir 206, which then drives fluid into the inflatable implant 202, which increases the pressure of the inflatable implant 202. This increase in pressure of the inflatable implant 202 further constricts the urethra and counters the additional push to the urine in the urethra caused by the increased pressure of the bladder. As a result, incontinence caused by the abdominal disturbance can be prevented.

Figure 4:
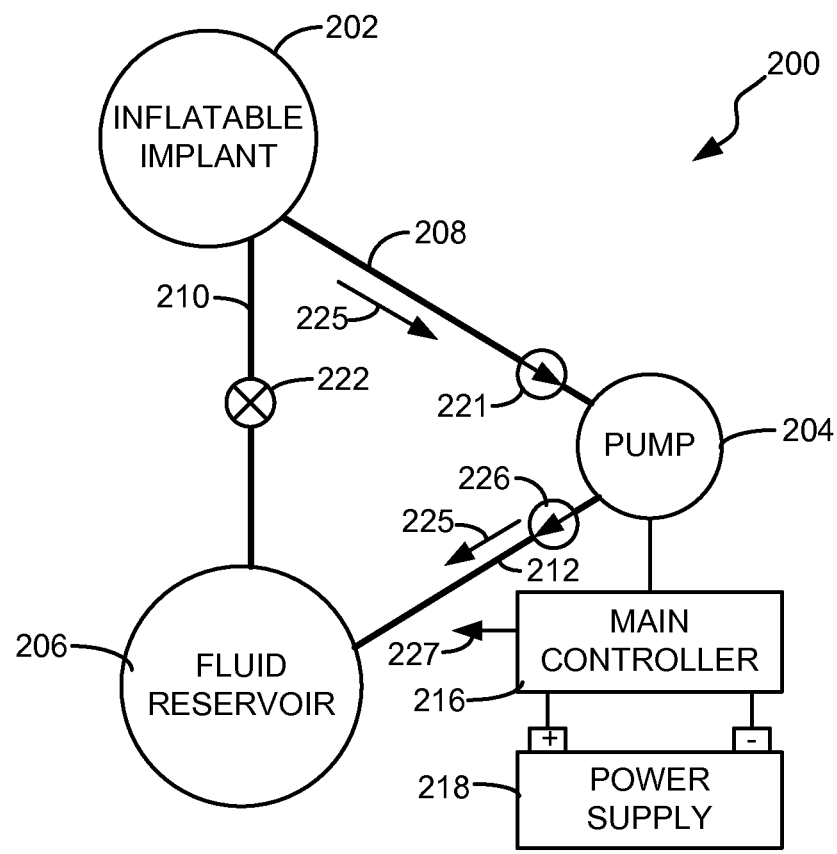

In one embodiment of the emptying state of the first configuration of the system 200, shown in FIG. 4, the valve 222 is set to the closed position, the valve 226 is opened, and the pump 204 is activated to drive the flow of fluid from the implant in the direction indicated by arrows 225. More specifically, the pump 204 drives a flow of fluid from the inflatable implant 202 into the first fluid path 208, through the valve 221, into the third fluid path 212, through the valve 226, and into the reservoir 206. As a result, the inflatable implant 202 deflates and the reservoir 206 inflates and becomes pressurized relative to the inflatable implant 202 to enable the refilling of the inflatable implant 202 when the system returns to the filling state (FIG. 3).

One embodiment of the first configuration of system 200 includes an emptied state, in which the valve 222 is in the closed position and the pump 204 is deactivated. The system 200 is set in the emptied state following the emptying state, in which the pressure of the inflatable implant 202 is decreased to a desired deflated pressure or the volume of the inflatable implant 202 is decreased to a desired deflated volume. The system 200 can be placed in the emptied state for extended periods of time because it does not require the use of electrical power from the supply 218. When the inflatable implant 202 is in the form of a cuff, the resultant relaxation of the pressure on the duct from the inflatable implant 202 can decrease tissue erosion of the duct.

Figure 5:
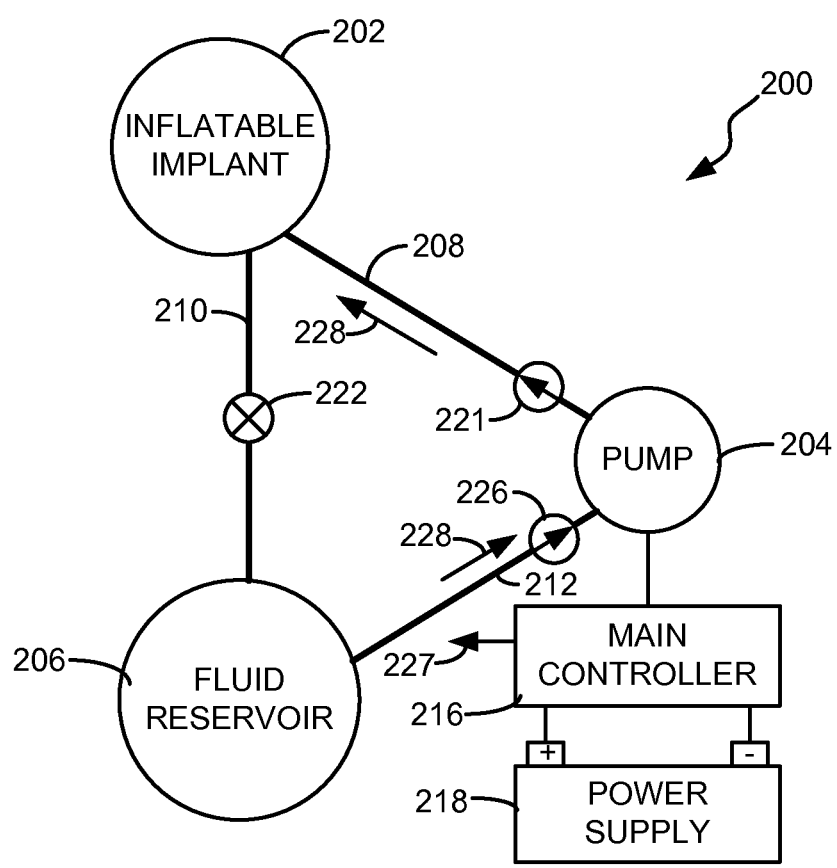
FIGS. 5 and 6 are simplified diagrams of a second configuration of the inflatable medical implant system in a filling state and an emptying state, respectively, in accordance with embodiments of the invention.

Embodiments of the filling and emptying states of the second configuration of the system 200 will be respectively described with reference to the simplified diagrams provided in FIGS. 5 and 6. In one embodiment of the filling state shown in FIG. 5, the pump 204 is activated and the valve 222 is set to the closed position, in which fluid is blocked from traveling between the inflatable implant 202 and the fluid reservoir 206 in the second fluid path 210. The pump 204 drives the fluid from the reservoir 206 into the third fluid path 212 and into the first fluid path 208 into the inflatable implant 202 as indicated by arrows 228. In one embodiment, the system 200 includes a valve 221, such as a check valve, that prevents the backflow of fluid toward the pump 204. Accordingly, during the filling state, the fluid reservoir 206 is deflated of fluid while the inflatable implant 202 is inflated.

When the pump 204 is deactivated by the controller 216, the system 200 enters an inflated or filled state where the inflatable implant 202 is maintained at a desired inflated pressure or volume because the fluid within the inflatable implant is prevented from flowing back toward the pump through the first fluid path 208 due to the valve 221, and the fluid in the inflatable implant 202 is prevented from flowing to the fluid reservoir 206 through the second fluid path 210 due to the closed valve 222.

Figure 6:
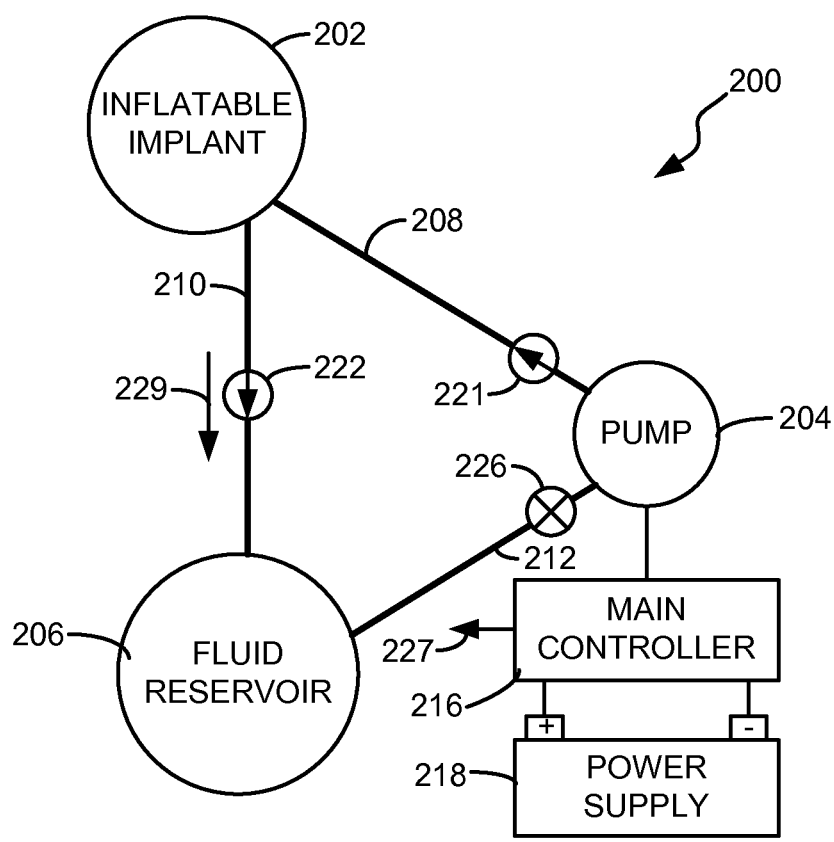

In one embodiment of the emptying state of the second configuration of the system 200, shown in FIG. 6, the valve 222 is set to the opened position, the pump 204 is deactivated and the valve 226 is actuated to the closed position. A flow of fluid from the inflatable implant 202 is driven in the direction indicated by arrow 229 into the second fluid path 210, through the valve 222 and into the fluid reservoir 206 in response to a pressure difference between the inflatable implant 202 and the fluid reservoir 206. Eventually, the flow of fluid through the second fluid path 210 stops when the pressures in the inflatable implant 202 and the fluid reservoir 206 become balanced. In one embodiment, the valve 222 is a check valve that prevents the backflow of fluid from the reservoir 206 to the implant 202. Accordingly, the implant can be further deflated by squeezing the implant, which drives additional fluid from the implant 202, past the check valve 222 and into the reservoir 206.

One embodiment of the second configuration of system 200 includes an emptied state, in which the valve 222 is in the closed position, the pump 204 is deactivated and the valves 226 or 221 are closed. The system 200 is set in the emptied state following the emptying states, during which the pressure of the inflatable implant 202 is decreased to a desired deflated pressure or the volume of the inflatable implant 202 is decreased to a desired deflated volume. The system 200 can be placed in the emptied state for extended periods of time because it does not require the use of electrical power from the supply 218.

In one embodiment, the controller is configured to control the valves, such as valves 221, 222, and/or 226, and the pump 204 to selectively place the system 200 in the filling state, the emptying state or the emptied state. The controller 216 can be configured to transition the system 200 from the emptying state to the filling state, and transition the system 200 from the filling state to the emptying state, in various ways. In one embodiment, the controller 216 is configured to activate the pump 204 for a set period of time while in the emptying state (FIG. 4) of the first configuration of the system 200, and the filling state (FIG. 5) of the second configuration of the system 200. The run time for the pump 204 for the emptying state (FIG. 4) and the filling state (FIG. 5) can be adjusted in accordance with the size of the inflatable implant 202 and the volumetric flow rate of the fluid flow driven by the pump 204. In one embodiment of the first configuration of the system 200, the controller 216 automatically places the system 200 in the filling state (FIG. 3) after the system 200 has been in the emptying state (FIG. 4) for a predetermined period of time. In one embodiment of the second configuration of the system 200, the controller 216 automatically places the system 200 in the filled state after the system 200 has been in the filling state (FIG. 5) for a predetermined period of time.

Additional embodiments of the system 200 relate to the transitioning of the pump 204 from the activated state (FIGS. 4 and 5) to the corresponding deactivated state (FIGS. 3 and 6) in response to a pressure feedback signal that is indicative of the interior pressure of the inflatable implant 202, which is further indicative of whether the inflatable implant 202 has reached the desired inflated state or deflated state. In one embodiment, the controller 216 deactivates the pump 204 when the pressure feedback signal indicates that the inflatable implant 202 has reached the desired deflated state during the emptying state (FIG. 4) for the first configuration of the system 200, or the desired inflated state during the inflating state (FIG. 5) for the second configuration of the system 200. In one embodiment, upon deactivating the pump 204, the first configuration of the system 200 is placed in the deflated state, and the second configuration of the system 200 is placed in the inflated state. Exemplary embodiments of the pressure feedback signal are described below.

In one embodiment, the system 200 comprises a pressure sensor 230, which directly measures the interior pressure in the inflatable implant 202, or indirectly measures the interior pressure of the inflatable implant 202 by sensing the pressure in the first fluid path 208, the second fluid path 210 or the third fluid path 212, from which the pressure of the inflatable implant 202 can be estimated. The pressure sensor 230 produces the pressure feedback signal 232 (FIG. 2) that is indicative of the sensed pressure and can be analyzed to determine whether the inflatable implant 202 has reached the desired deflated or inflated state.

In one embodiment, the controller 216 compares the sensed pressure value indicated by the signal 232 to an empirically set threshold value that corresponds to the value indicated by the signal 232 when the inflatable implant 202 is in the desired deflated or inflated state. Alternatively, the empirically set threshold can correspond to a maximum pressure that the inflatable implant 202 is desired to have. The controller 216 deactivates the pump when the value indicated by the signal 232 reaches (e.g., exceeds) the threshold value.

In accordance with another embodiment, the controller 216 samples the sensed pressure value indicated by the signal 232 and compares the change in the sensed pressure value over a predetermined period of time to an empirically set threshold change in value, which corresponds to the inflatable implant 202 reaching the desired deflated or inflated state. When the change in the sensed pressure value reaches (e.g., exceeds) the threshold change in value, the controller deactivates the pump 204.

In accordance with another embodiment, the system 200 comprises a current sensor or voltage sensor, which are both represented by box 234 in FIG. 2 in order to simplify the drawing. The current sensor measures the current drawn by the pump 204 during activation periods and produces an output signal 236 that is indicative of the magnitude of the sensed current. The voltage sensor measures the voltage supplied to the pump 204 during activation periods and produces an output signal 236 that is indicative of the magnitude of the sensed voltage.

When the inflatable implant 202 is substantially depleted of fluid (i.e., deflated state) or when the inflatable implant 202 is substantially filled with fluid (i.e., inflated state), the current drawn by the pump will increase dramatically. Accordingly, the amount of current fed to the pump can be used to indicate the pressure of the inflatable implant 202 and whether the inflatable implant 202 has reached the desired deflated state while the system 200 (first configuration) is in the emptying state (FIG. 4), or whether the inflatable implant 202 has reached the desired inflated state while the system 200 (second configuration) is in the filling state (FIG. 5). Thus, the signal 236 from the current sensor 234 can operate as the pressure feedback signal.

In one embodiment, the controller 216 compares the sensed current value indicated by the signal 236 to an empirically set threshold value, which corresponds to the inflatable implant 202 reaching the desired deflated or inflated state. When the sensed current value reaches (e.g., exceeds) the threshold value, the controller 216 deactivates the pump 204.

In accordance with another embodiment, the controller 216 samples the sensed current value indicated by the signal 236 and compares the change in the sensed current value over a predetermined period of time to an empirically set threshold change in value, which corresponds to the inflatable implant 202 reaching the desired deflated or inflated state. When the change in the sensed current value reaches (e.g., exceeds) the threshold change in value, the controller deactivates the pump 204.

It has also been recognized that the voltage supplied to the pump 204 from the power supply 218 generally determines the maximum and minimum pressures that can be generated by the pump in the first fluid path and, thus, the inflatable implant 202 over a specified period of time. That is, the resultant pressure of the inflatable implant 202 from operating the pump 204 can be estimated by the voltage supplied to the pump 204 and the length of the time that the pump 204 is activated. Thus, the signal 236 from the voltage sensor 234 can operate as the pressure feedback signal, from which interior pressure and state (i.e., desired inflated or deflated state) of the inflatable implant 202 can be estimated. In one embodiment, upon activation of the pump 204, the controller 216 compares the sensed voltage value indicated by the signal 236 to values stored in a look-up table. The lookup table provides a runtime that the pump should be activated to reach the desired deflated or inflated state. The controller 116 deactivates the pump upon expiration of the runtime to place the inflatable implant 202 in the desired deflated or inflated state.

One embodiment of the system 200 includes a state controller 240, shown in FIG. 2, that is configured to generate state commands, represented by signal 242. In one embodiment, the controller 216 places the system 200 in the filling state, the filled state, the emptying stated, or the emptied state, in response to the state commands 242.

Figure 7:
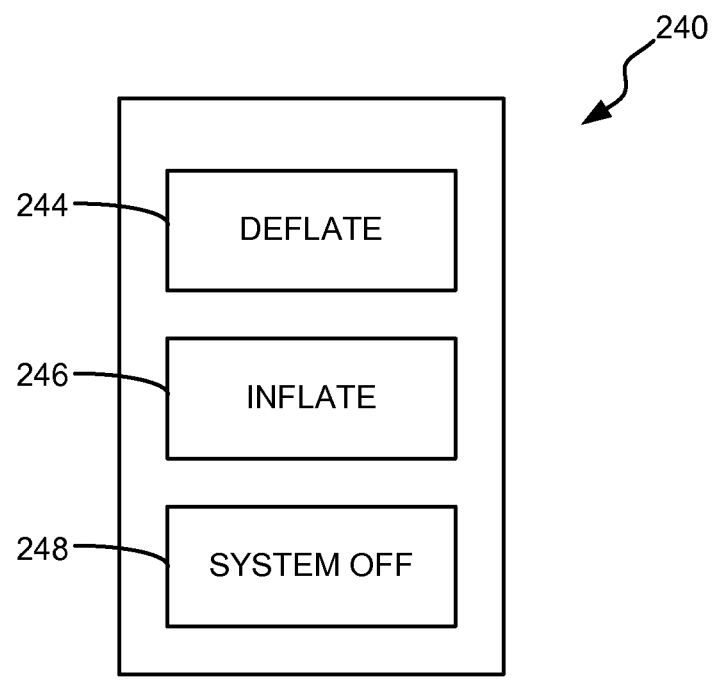
FIG. 7 is a simplified diagram of a state controller in accordance with embodiments of the invention.

FIG. 7 is a simplified diagram of the state controller 240 in accordance with embodiments of the invention. In one embodiment, the state controller 240 is an external device, such as a key fob, that the patient can use to place the system 200 in the desired state. In one embodiment, the state commands 242 are transmitted wirelessly to the controller 216 in response to a user input. In one embodiment, the controller 216 performs a control function responsive to the received state command 242. Exemplary control functions include activating the pump 204, deactivating the pump 204, actuating the valve 222 to the opened position using the electrical control signal 227, or actuating the valve 222 to the closed position using the control signal 227.

In accordance with another embodiment, the controller 216 places the system 200 in one of the filling, filled, emptying, or emptied states in response to the received state command 242. In one embodiment, the state controller 240 includes a "DEFLATE" button 244, which, when pressed by the user, transmits a state command 242 to the controller 216 and the controller 216 places the system 200 in the emptying state (FIGS. 4 and 6) in response to the received state command 242. In another embodiment, the state controller 240 includes an "INFLATE" button 246, which, when pressed by the user, causes the state controller 240 to transmit a state command 242 to the controller 216 and the controller places the system 200 in the filling state (FIGS. 3 AND 5) in response to the state command 242. Of course, the button 246 is unnecessary when the controller 216 is configured to set the system 200 in the filling state automatically following the expiration of a predetermined period of time after the placement of the system 200 in the emptying state.

In accordance with another embodiment, the state controller 240 includes a "SYSTEM OFF" button 248, which, when pressed by the user, transmits a state command 242 to the controller 216 and the controller 216 to deactivate the pump 204 and maintain the inflatable implant 202 in the current deflated or inflated state by, for example, closing valve 222. Thus, the "SYSTEM OFF" button 248 can place the system 200 in the filled or emptied states.

In one embodiment, the state controller 240 is implanted in the patient at a location that is accessible by the patient, such as the scrotum of a male patient. The state controller 240 communicates with the controller 216 either wirelessly or through a wired connection. In one embodiment, the state controller 240 comprises one or more buttons that the patient can locate, and distinguish the individual buttons from the others, by feel. In one embodiment, the state controller 240 comprises a button, depressions of which cause the state controller 240 to cycle through two or more of the state commands (e.g., filling state, the filled state, the emptying stated, or the emptied state) in a desired order, which are delivered to the controller 116 as signals 242. This allows the state controller to have only a single button while providing the patient a full range of commands for the system 200.

Another embodiment of the invention is directed to a surgical kit comprising the inflatable implant 202, the pump 204, the reservoir 206, the controller 216, and the power supply 218. In one embodiment, the kit further comprises valve 221, valve 222 and/or valve 226, each of which may be integrated with, or attached to, one of the other components of the system 200 provided in the kit, such as with the pump 204. In one embodiment, the kit includes tubing to form the first fluid path 208, the second fluid path 210 and the third fluid path 212.

The components of the kit are preferably sterilized and sealed in a container, such as a bag. In one embodiment, the components of the kit are coated with an antibacterial coating, such as InhibiZone Antibiotic Surface Treatment, a proprietary combination of rifampin and minocycline.

Figure 8:
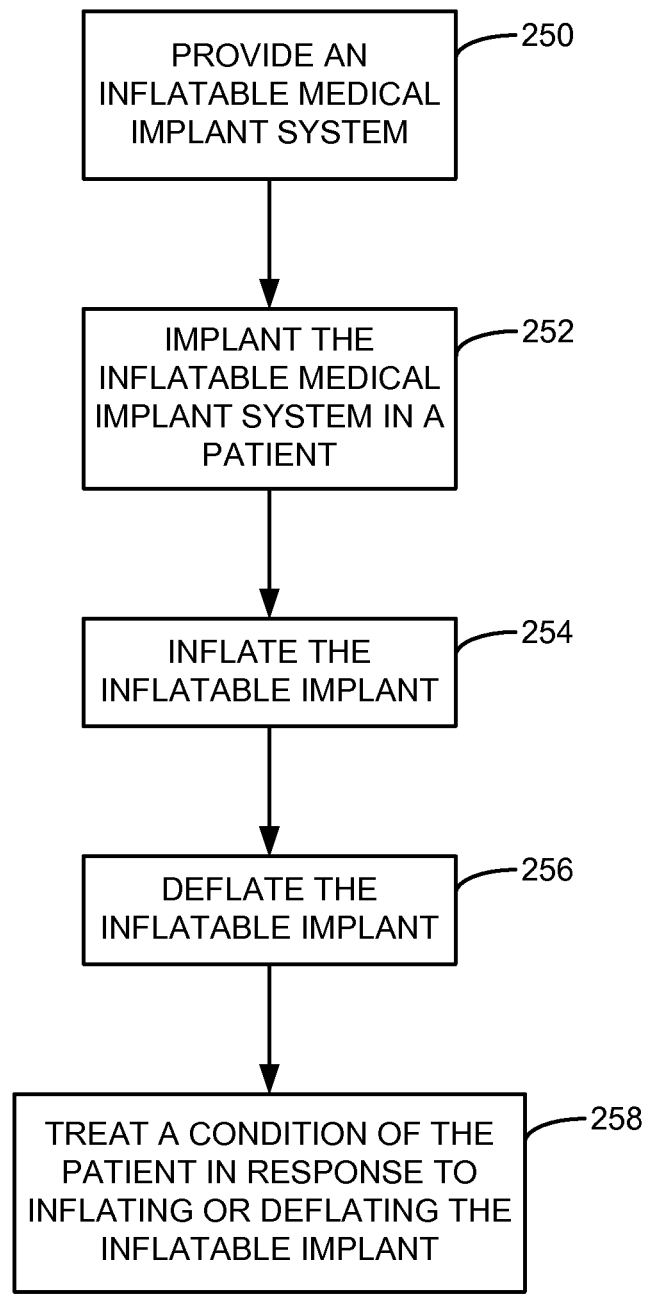
FIG. 8 is a flowchart illustrating a method in accordance with embodiments of the invention.

Yet another embodiment of the invention is directed to the method illustrated in the flowchart of FIG. 8. At step 250 of the method, an inflatable medical implant system 200 (FIG. 2), in accordance with one or more of the embodiments described above, is provided. In one embodiment, step 250 comprises providing: an inflatable implant 202; a pump 204; a reservoir 206; a first fluid path 208 between the inflatable implant and the pump; a second fluid path 210 between the inflatable implant and the reservoir; a third fluid path 212 between the reservoir and the pump; a valve 222 in the second fluid path having an opened position, in which fluid is free to travel between the reservoir and the inflatable implant through the second fluid path, and a closed position, in which fluid is blocked from traveling between the reservoir and the inflatable implant through the second fluid path; a controller 216 configured to control the pump and selectively actuate the valve between the opened and closed positions; and an implantable power supply that provides electrical power to the pump. In one embodiment, the system 200 is provided in the form of a surgical kit, as described above.

At step 252, of the method, the inflatable medical implant system 200 is implanted in a male or female patient in accordance with conventional surgical techniques.

In one embodiment of the method, the system 200 is operated while implanted in the patient to treat a condition of the patient. Embodiments of this method step comprise inflating the inflatable implant 202, as indicated at step 254, by either placing the valve 222 in the opened position and driving a flow of fluid from the reservoir 206 into the inflatable implant 202 through the second fluid path 210 in response to a pressure difference between the reservoir 206 and the inflatable implant 202, or placing the valve 222 in the closed position and driving a flow of fluid from the first fluid path into the inflatable implant 202 using the pump 204. Another embodiment of operating of the system 200 while implanted in the patient comprises deflating the inflatable implant 202, as indicated at step 256, by either placing the valve 222 in the closed position and driving a flow of fluid from inflatable implant 202 into the first fluid path 208 using the pump 204, or placing the valve 222 in the opened position and driving a flow of fluid from the inflatable implant 202 into the reservoir 206 through the second fluid path 210 in response to a pressure difference between the implant 202 and the reservoir 206. In one embodiment, the medical condition of the patient is treated in response to the inflation the inflatable implant 202 and/or the deflation the inflatable implant 202, as indicated at step 258. Embodiments of the medical condition include urinary incontinence and fecal incontinence.

In one embodiment of the method, a pressure feedback signal, such as signal 232 or 236 (FIG. 2), is generated in response to driving fluid through the first fluid path 208 using the pump 204. The pressure feedback signal is indicative of the pressure of the inflatable implant 202. The pump 204 is deactivated using the controller 216 in response to the pressure feedback signal. In one embodiment, the pressure feedback signal 236 is generated responsive to a sensed current by a current sensor 234. In one embodiment, the pressure feedback signal 236 is generated responsive to a sensed voltage by a voltage sensor 234. In another embodiment, the pressure feedback signal 232 is generated responsive to a sensed pressure by a pressure sensor 230.

In one embodiment of the method, the inflatable implant comprises an inflatable cuff or an inflatable penile prosthesis. In one embodiment, the inflatable cuff is implanted around the urethra of the patient. In another embodiment, the inflatable cuff is implanted around the colon or rectum of the patient. In one embodiment, the inflatable cuff is implanted for use as a gastric cuff to control weight loss dynamically. In one embodiment, the inflatable cuff is implanted for use as a stoma clamp/cuff on the intestine or colon of the patient where portions have been removed.

In accordance with the above discussion, one embodiment of the invention is directed to a method comprising:

providing (250) an inflatable medical implant system (200) comprising an inflatable implant (202); a pump (204); a reservoir (206); a first fluid path (208) between the inflatable implant and the pump; a second fluid path (210) between the inflatable implant and the reservoir; a third fluid path (212) between the reservoir and the pump; a valve (222) in the second fluid path having an opened position, in which fluid is free to travel between the reservoir and the inflatable implant through the second fluid path, and a closed position, in which fluid is blocked from traveling between the reservoir and the inflatable implant through the second fluid path; a controller (216) configured to control the pump and selectively actuate the valve between the opened and closed positions; and an implantable power supply (218) that provides electrical power to the pump;

implanting (252) the inflatable medical implant system in a patient;

inflating (254) the inflatable implant comprising one of:

placing the valve in the opened position and driving a flow of fluid from the reservoir into the inflatable implant through the second fluid path in response to a pressure difference between the reservoir and the inflatable implant; and placing the valve in the closed position and driving a flow of fluid from the first fluid path into the inflatable implant using the pump;

deflating (256) the inflatable implant comprising one of:

placing the valve in the closed position and driving a flow of fluid from inflatable implant into the first fluid path using the pump; and placing the valve in the opened position and driving a flow of fluid from the inflatable implant into the reservoir through the second fluid path in response to a pressure difference between the implant and the reservoir; and treating (258) a medical condition of the patient in response to at least one of inflating the inflatable implant and deflating the inflatable implant.

In one embodiment, the method further comprises:

generating a pressure feedback signal (232 or 236) in response to driving fluid through the first fluid path using the pump, wherein the pressure feedback signal is indicative of a pressure of the inflatable implant; and deactivating the pump using the controller responsive to the pressure feedback signal.

One embodiment of generating a pressure feedback signal comprises at least one method step selected from the group consisting of:

sensing a current provided to the pump and generating the pressure feedback signal (236) responsive to the sensed current; and sensing a voltage supplied to the pump and generating the pressure feedback signal (236) responsive to the sensed voltage.

One embodiment of providing an inflatable medical implant system comprises providing an inflatable implant selected from the group consisting of an inflatable cuff and a penile prosthesis.

Although the present invention has been described with reference to preferred embodiments, workers skilled in the art will recognize that changes may be made in form and detail without departing from the spirit and scope of the invention.

What is claimed is:

1. An inflatable medical implant system configured for implantation in a patient comprising:

a first fluid path;

an inflatable implant in fluid communication with the first fluid path, wherein the inflatable implant is configured to serve a medical purpose;

an electric pump in fluid communication with the first fluid path;
an implantable power supply that provides electrical power to the pump;
a sensor configured to sense one of a current and a voltage supplied to the pump and output a pressure feedback signal that is indicative of a pressure of the inflatable implant; and
a controller electrically coupled to the pump and configured to activate the pump to drive a flow of fluid through the first fluid path and deactivate the pump responsive to the pressure feedback signal.

2. The system of claim 1 further comprising:
a second fluid path in fluid communication with the inflatable implant;
a third fluid path in fluid communication with the pump;
a reservoir in fluid communication with the second fluid path and the third fluid path; and
a valve in line with the second fluid path between the inflatable implant and the reservoir, the valve having an opened position, in which fluid is free to travel between the reservoir and the inflatable implant through the second fluid path, and a closed position, in which fluid is blocked from traveling between the reservoir and the inflatable implant through the second fluid path;
wherein the controller generates an electrical control signal to selectively actuate the valve to the opened and closed positions.

3. The system of claim 2, wherein the inflatable implant is selected from the group consisting of an inflatable cuff and a penile prosthesis.

4. The system of claim 3, wherein the system comprises an implant filling state, in which the valve is in the opened position, the pump is deactivated, and the reservoir drives a flow of fluid from the reservoir into the inflatable implant through the second fluid path in response to a pressure difference between the reservoir and the inflatable implant, whereby the inflatable implant inflates.

5. The system of claim 4, wherein the system comprises an implant emptying state, in which the valve is in the closed position and the pump is activated to drive a flow of fluid from the inflatable implant into the first fluid path, whereby the inflatable implant deflates.

6. The system of claim 4, wherein the system comprises an implant emptying state, in which the valve is in the opened position and the pump is deactivated, and the inflatable implant drives a flow of fluid from the inflatable implant into the reservoir through the second fluid path in response to a pressure difference between the implant and the reservoir, whereby the inflatable implant deflates.

7. The system of claim 3, wherein the system comprises an implant filling state, in which the valve is in the closed position and the pump is activated to drive a flow of fluid from the reservoir into the first fluid path, whereby the inflatable implant inflates.

8. The system of claim 1, wherein:
the system further comprises a state controller that wirelessly transmits state commands responsive to a user input from the state controller; and
the controller receives the state commands and performs a control function selected from the group consisting of:
activating the pump;
deactivating the pump;
actuating the valve to an opened position using an electrical control signal; and
actuating the valve to a closed position using a control signal.

9. An inflatable medical implant system for implantation in a patient comprising:
an inflatable implant selected from the group consisting of an inflatable cuff and a penile prosthesis;
an electric pump;
an implantable power supply that provides electrical power to the pump;
a first fluid path between the inflatable implant and the pump, wherein the first fluid path provides fluid communication between the inflatable implant and the pump;
a reservoir;
a second fluid path between the inflatable implant and the reservoir, wherein the second fluid path provides fluid communication between the inflatable implant and the reservoir;
a third fluid path between the pump and the reservoir, wherein the third fluid path provides fluid communication between the pump and the reservoir;
a valve in line with the second fluid path between the inflatable implant and the reservoir, the valve having an opened position, in which fluid is free to travel between the reservoir and the inflatable implant through the second fluid path, and a closed position, in which fluid is blocked from traveling between the reservoir and the inflatable implant through the second fluid path;
a sensor configured to sense one of a current and a voltage supplied to the pump and output a, pressure feedback signal that is indicative of a pressure of the inflatable implant; and
a controller electrically coupled to the pump and configured to control the pump responsive to the pressure feedback signal, and generate an electrical control signal that selectively actuates the valve to the opened and closed positions.

10. The system of claim 9, further comprising:
a filling state, in which the valve is in the opened position, the pump is deactivated and the reservoir drives a flow of fluid from the reservoir into the inflatable implant through the second fluid path in response to a pressure difference between the reservoir and the inflatable implant, whereby the inflatable implant inflates; and
an emptying state, in which the valve is in the closed position and the pump is activated to drive a flow of fluid from the inflatable implant into the first fluid path, whereby the inflatable implant deflates;
wherein the controller is configured to control the valve and the pump to selectively place the system in one of the filling state and the emptying state.

11. The system of claim 9, further comprising:
a filling state, in which the valve is in the closed position and the pump is activated to drive a flow of fluid from the first fluid path into the inflatable implant, whereby the inflatable implant inflates; and
an emptying state, in which the valve is in the opened position, the pump is deactivated, and the inflatable implant drives a flow of fluid from the inflatable implant into the reservoir through the second fluid path in response to a pressure difference between the implant and the reservoir, whereby the inflatable implant deflates;
wherein the controller is configured to control the valve and the pump to selectively place the system in one of the filling state and the emptying state.

* * * * *

UNITED STATES PATENT AND TRADEMARK OFFICE
CERTIFICATE OF CORRECTION

Page 1 of 1

PATENT NO.      : 8,585,580 B2
APPLICATION NO. : 12/864315
DATED           : November 19, 2013
INVENTOR(S)     : Shay Moshe Vaingast and Charles C. Kuyava It is certified that error appears in the above-identified patent and that said Letters Patent is hereby corrected as shown below:

On the Title Page

Item (57) ABSTRACT in the second to the last sentence, delete "and", insert --an--.

In the Claims

Column 14, line 29, delete "," between "a" and "pressure".

Signed and Sealed this
First Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,585,580 B2  
APPLICATION NO.  : 12/864315  
DATED            : November 19, 2013  
INVENTOR(S)      : Vaingast et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 571 days.

Signed and Sealed this
Twenty-second Day of September, 2015

Michelle K. Lee
*Director of the United States Patent and Trademark Office*